US00PP21759P2

(12) United States Plant Patent
Dofferhoff

(10) Patent No.: US PP21,759 P2
(45) Date of Patent: Mar. 1, 2011

(54) ***GENTIANA* PLANT NAMED 'WHITE MAGIC'**

(50) Latin Name: *Gentiana makinoi*
Varietal Denomination: White Magic

(76) Inventor: Hans Dofferhoff, Reeuwijk (NL)

( * ) Notice: Subject to any disclaimer, the term of this patent is extended or adjusted under 35 U.S.C. 154(b) by 0 days.

(21) Appl. No.: 12/590,693

(22) Filed: Nov. 12, 2009

(51) Int. Cl.
*A01H 5/00* (2006.01)

(52) U.S. Cl. ..... Plt./433
(58) Field of Classification Search ..... Plt./433
See application file for complete search history.

*Primary Examiner*—Kent L Bell
(74) *Attorney, Agent, or Firm*—Penny J. Aguirre

(57) ABSTRACT

A new cultivar of *Gentiana makinoi* named 'White Magic', characterized by its flowers that are clear white in color with specs of yellow-green, its dwarf and compact plant habit, and its abundance of flowers produced from May to September in The Netherlands if spent blooms are removed.

2 Drawing Sheets

Botanical classification: *Gentiana makinoi.*
Varietal denomination: 'White Magic'.

BACKGROUND OF THE INVENTION

The present invention relates to a new and distinct cultivar of *Gentiana makinoi* and will be referred to hereafter by its cultivar name, 'White Magic'. 'White Magic' represents a new Gentian, an herbaceous perennial grown for landscape use.

The Inventor discovered the new cultivar, 'White Magic', as a naturally occurring branch mutation of 'Blue Magic' (U.S. Plant Pat. No. 20,704) during crop production in a greenhouse in Reeuwijk, The Netherlands in the summer of 2008.

Asexual reproduction of the new cultivar was first accomplished by in vitro propagation under the direction of the Inventor in Rijswijk, The Netherlands in January 2009. It has been determined that the characteristics of the new cultivar are stable and are reproduced true to type in successive generations.

The following traits have been repeatedly observed and represent the characteristics of the new cultivar after observing plants grown outdoors in a field for two years in Reeuwijk, The Netherlands. These attributes in combination distinguish 'White Magic' from all other cultivars of *Gentiana* known to the Inventor.

1. 'White Magic' exhibits flowers that are clear white in color with specs of yellow-green.
2. 'White Magic' exhibits a dwarf and compact plant habit.
3. 'White Magic' exhibits an abundance of flowers.
4. 'White Magic' blooms from May to September in The Netherlands if spent blooms are removed.

'White Magic' differs from its parent plant, 'Blue Magic' in having flowers that are white in color and in having a longer bloom season. 'White Magic' can also be compared to 'Magic Purple' (U.S. Plant Pat. No. 19,809) and 'Marsha' (U.S. Plant Pat. No. 16,562) which are similar in flower form. Both cultivars differ from 'White Magic' in having purple flowers and are not as compact in habit. There are no other cultivars or varieties of *Gentiana* with white flowers known to the Inventor that are similar to 'White Magic'.

BRIEF DESCRIPTION OF THE PHOTOGRAPHS

The plants and plant parts in the photographs were taken of an 18 month-old plant of 'White Magic' as grown in a 15-cm container in an open greenhouse in Reeuwijk, The Netherlands.

Figure 1:
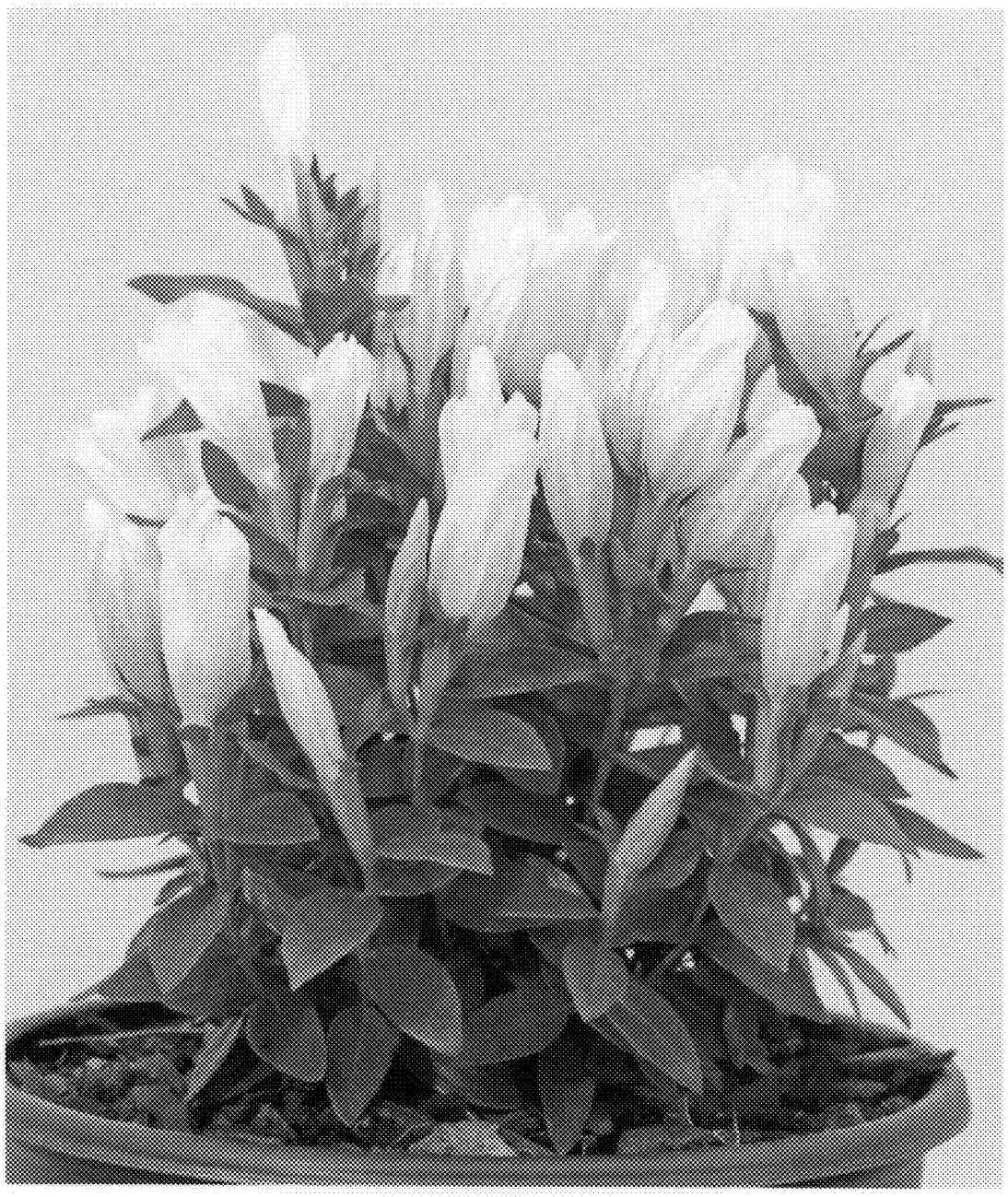

The photograph in FIG. 1 provides a side view of 'White Magic' in bloom.

Figure 2:
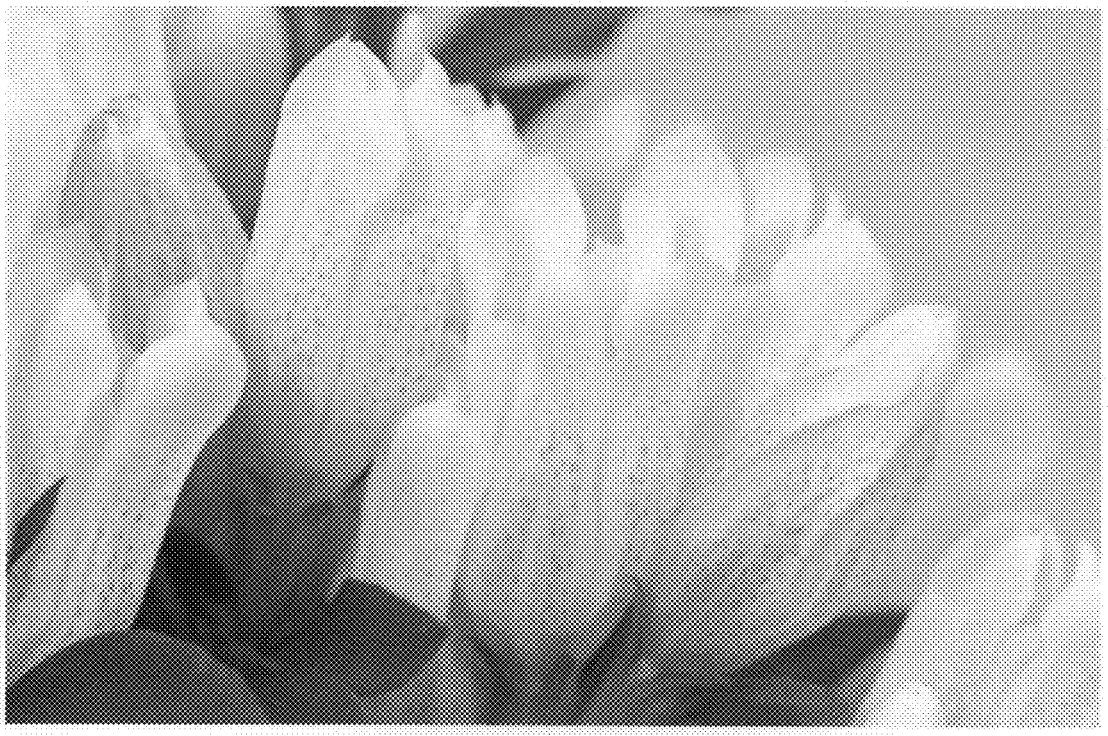

The photograph in FIG. 2 provides a close-up view of flowers of 'White Magic'.

Figure 3:
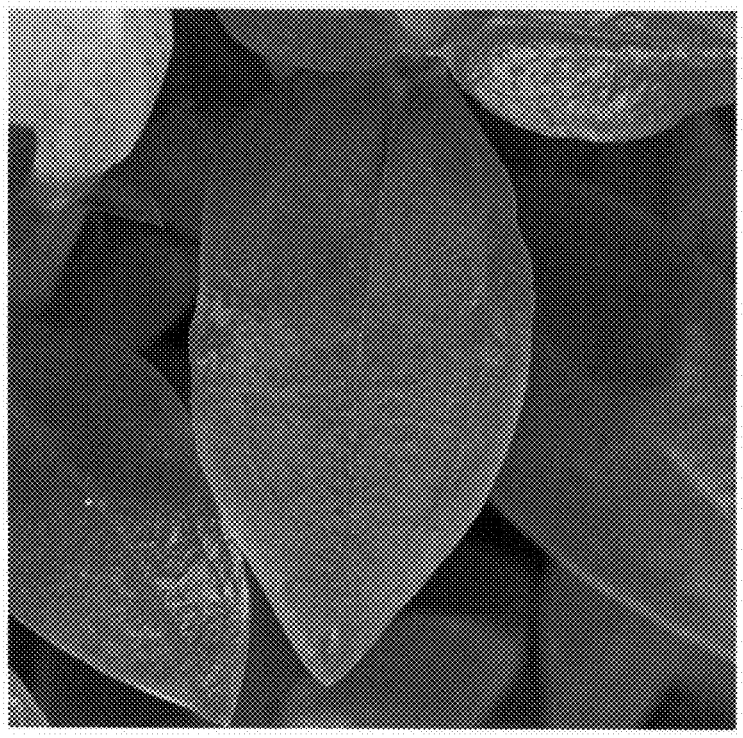

The photograph in FIG. 3 provides a close-up view of a leaf of 'White Magic'.

The colors in the photograph may differ slightly from the color values cited in the detailed botanical description, which accurately describe the colors of the new *Gentiana.*

DETAILED BOTANICAL DESCRIPTION

The following is a detailed description of eighteen month-old plants the new cultivar as grown in 15-cm containers in Reeuwijk, The Netherlands under natural light in an open greenhouse with average day temperatures ranging from 14° to 32° C. and average night temperatures ranging from 6° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Continuously from May to September in The Netherlands if spent blooms are removed.

*Plant type.*—Herbaceous perennial.

*Plant habit.*—Clump-forming, upright, compact, uniform.

*Height and spread.*—Average of 15.4 cm in height and 17.8 cm in spread.

*Cold hardiness.*—At least to U.S.D.A. Zone 6.

*Heat tolerance.*—At least to 35° C.

*Diseases and pests.*—Not more susceptible than other cultivars of *Gentiana makinoi.*

*Root description.*—Fine.

Growth and propagation:

*Propagation.*—Stem cuttings and tissue culture.

*Root development.*—Roots fully develop in a 9 cm pots in about 3 months from a rooted transplant from tissue culture.

*Growth rate.*—Moderately vigorous, growing about 8 cm per month during the growing season.

Stem description:

*Stem shape.*—Round.

*Stem color.*—144D.

*Stem size.*—Lateral branches; an average of 7.5 cm in length, average of 1.5 mm in diameter.

*Stem surface.*—Slightly glossy, smooth.

*Stem aspect.*—Upright, strong.

*Internode length.*—Average of 1.6 cm.

*Branching habit.*—Basal branching, about 2 un-branched stems emerge from each main stem.

Foliage description:

*Leaf shape.*—Elliptic to ovate.

*Leaf division.*—Simple.

*Leaf base.*—Cuneate.

*Leaf apex.*—Acute.

*Leaf venation.*—Pinnate, only midrib is conspicuous, color on upper surface is 144A to 144B, color on lower surface is 144B to 144C.

*Leaf margins.*—Entire.

*Leaf attachment.*—Sessile.

*Leaf arrangement.*—Opposite.

*Leaf surface.*—Dull, slightly leathery and glabrous on upper and lower surface.

*Leaf color.*—Young upper surface; 143A, young lower surface; ranges from 143C to 144A, mature upper surface; N137D, mature lower surface; ranges from 146A to 146B.

*Leaf number.*—An average of 8 per lateral branch.

*Leaf size.*—Average of 2.8 cm in length and 1.6 cm in width.

*Leaf substance.*—Moderate durability to environmental stresses.

Flower description:

*Flower type.*—Axillary and terminal tubular flowers, arising singularly or in pairs or clusters of 3.

*Flower cluster size.*—Average of 7 cm in width and diameter when in clusters of 3.

*Flower fragrance.*—Moderate, cinnamon-like scent.

*Flower lastingness.*—Average of 10 days on plant and 14 days as a cut flower, persistent.

*Flower bud description.*—Narrowly elliptic in shape, an average of 1.4 cm in diameter and 3.5 cm in length, color ranges from 145B to 145D with immature calyx portion ranging from 145A to 144A.

*Flower quantity.*—Average of 3 per lateral stem, an average of 128 per 15-cm container.

*Flower aspect.*—Upright.

*Flower shape.*—Tubular.

*Flower size.*—4.6 cm in depth and 2 cm in diameter.

*Rate of opening.*—About 50% fully open at flowering peak.

*Pedicels.*—Average of 0.4 cm in length and 1.5 mm in diameter, held upright, 144A in color.

*Peduncles.*—None, pedicels are attached to stem at terminus or axillary node.

*Petals.*—5, about 4.4 cm in length and 8 mm in width, oblong in shape, 85% of lower portion is fused into a tubular shape, margin is entire, apex is broadly acute, surface is smooth and slightly glossy in appearance, color (opening and fully open); outer surface N155D dotted with 145C and base 145D, inner surface (opening and fully open); N155D and base 145C to 145D.

*Calyx form.*—Campanulate in form, average of 2 cm in length and 2.2 cm in diameter.

*Sepals.*—5, an average of 2 cm in length and 3 mm in width, base fused with free tips linear in shape, margin is entire, apex is narrowly acute, base is fused, surface is smooth and dull in appearance, color of inner surface ranges from 145A to 144A, color of outer surface ranges from 145D to 143A.

Reproductive organs:

*Gynoecium.*—1 pistil, about 3.1 cm in length, stigma is linear and decurrent when ovary develops and 150C in color, style is about 2.9 cm in length and 145B in color, ovary is 145B in color.

*Androecium.*—5 stamens, anthers are oblong in shape, basifixed, about 2.5 mm in length and 4C in color, filaments are about 2.5 cm in length and 155C in color on upper portion and 145B in color on lower portion, pollen is low in quantity and 4B in color.

*Seed.*—No seed production has been observed under the conditions tested.

It is claimed:

1. A new and distinct cultivar of *Gentiana makinoi* plant named 'White Magic' as herein illustrated and described.

* * * * *